US012747471B2

(12) United States Patent
Rezaei et al.

(10) Patent No.: US 12,747,471 B2
(45) Date of Patent: Sep. 29, 2026

(54) CIRCUIT DESIGN TO APPLY DIFFERENT VOLTAGES IN A NANOPORE ARRAY

(71) Applicant: Illumina, Inc., San Diego, CA (US)

(72) Inventors: Mohsen Rezaei, Brown Deer, WI (US); Xu Liu, Foster City, CA (US); Arvin Emadi, Hayward, CA (US)

(73) Assignee: ILLUMINA, INC., San Diego, CA (US)

( * ) Notice: Subject to any disclaimer, the term of this patent is extended or adjusted under 35 U.S.C. 154(b) by 966 days.

(21) Appl. No.: 17/930,673

(22) Filed: Sep. 8, 2022

(65) Prior Publication Data

US 2023/0070552 A1 Mar. 9, 2023

Related U.S. Application Data

(60) Provisional application No. 63/261,059, filed on Sep. 9, 2021.

(51) Int. Cl.
*C12Q 1/6869* (2018.01)
*G01N 33/487* (2006.01)

(52) U.S. Cl.
CPC ..... *C12Q 1/6869* (2013.01); *G01N 33/48721* (2013.01)

(58) Field of Classification Search
CPC ........................ C12Q 1/6869; G01N 33/48721
See application file for complete search history.

(56) References Cited

U.S. PATENT DOCUMENTS

2014/0203464 A1* 7/2014 Chen ...................... G01N 15/12 425/4 R
2015/0377856 A1* 12/2015 Dunbar ............... H03F 3/45076 204/452
2016/0178554 A1* 6/2016 Chen ................ G01N 33/48721 204/603
2017/0091381 A1* 3/2017 Fernandez-Gomez ...................... G16B 30/00
2019/0369080 A1* 12/2019 Yanagawa ................. C25F 3/12

FOREIGN PATENT DOCUMENTS

CN 112994680 A * 6/2021 ......... H03K 19/0185
WO WO 22/005780 1/2022
WO WO 22/212038 10/2022

OTHER PUBLICATIONS

Wang et al., English translation of CN-112994680-A, 2021 (Year: 2021).*

* cited by examiner

*Primary Examiner* — Shizhi Qian
(74) *Attorney, Agent, or Firm* — Knobbe, Martens, Olson & Bear, LLP

(57) ABSTRACT

In one aspect, the disclosed technology relates to systems and methods for sequencing polynucleotides. In one embodiment, the disclosed system for sequencing polynucleotides includes: a sequencing cell comprising a nanopore for sensing a polynucleotide; an electronic circuit configured to measure an electrical response in the sequencing cell, the electronic circuit comprising an operational amplifier; and a memory unit configured to store a state of the sequencing cell.

18 Claims, 9 Drawing Sheets

CIRCUIT DESIGN TO APPLY DIFFERENT VOLTAGES IN A NANOPORE ARRAY

CROSS-REFERENCE TO RELATED APPLICATIONS

This application claims priority to U.S. Provisional Application No. 63/261,059, filed Sep. 9, 2021, the content of which is incorporated by reference in its entirety.

BACKGROUND

Some polynucleotide sequencing techniques involve performing a large number of controlled reactions on support surfaces or within predefined reaction chambers. The controlled reactions may then be observed or detected, and subsequent analysis may help identify properties of the polynucleotide involved in the reaction. Examples of such sequencing techniques include next-generation sequencing or massive parallel sequencing involving sequencing-by-ligation, sequencing-by-synthesis, reversible terminator chemistry, or pyrosequencing approaches.

Some polynucleotide sequencing techniques utilize a nanopore, which can provide a path for an ionic electrical current. For example, as the polynucleotide traverses through the nanopore, it influences the electrical current through the nanopore. Each passing nucleotide, or series of nucleotides, that passes through the nanopore yields a characteristic electrical current. These characteristic electrical currents of the traversing polynucleotide can be recorded to determine the sequence of the polynucleotide.

SUMMARY

Provided in examples herein are methods for sequencing biopolymers, particularly polynucleotides, and systems and kits for performing the methods.

The systems, devices, kits, and methods disclosed herein each have several aspects, no single one of which is solely responsible for their desirable attributes. Without limiting the scope of the claims, some prominent features will now be discussed briefly. Numerous other examples are also contemplated, including examples that have fewer, additional, and/or different components, steps, features, objects, benefits, and advantages. The components, aspects, and steps may also be arranged and ordered differently. After considering this discussion, and particularly after reading the section entitled "Detailed Description," one will understand how the features of the devices and methods disclosed herein provide advantages over other known devices and methods.

In some applications of nanopore nucleic acid sequencing, there is a need for applying different bias voltages to different unit cells in an array of nanopore unit cells (e.g., a 2D array of nanopore unit cells). In some embodiments, there is a need for dividing an array of nanopore unit cells into different subgroups based on the conditions of different nanopores, and for imposing different modes of operation on the different subgroups. In some embodiments, there is a need for independently changing the mode of operation in each nanopore unit cell.

In some embodiments, disclosed is a circuit design that can apply different bias voltages to different unit cells in an array of nanopore unit cells. In some embodiments, disclosed is a circuit design that can apply different bias voltages to different subgroups of unit cells in an array of nanopore unit cells. In some embodiments, disclosed is a memory cell or memory unit that is added to each nanopore unit cell and is used to store the state of each nanopore unit cell.

Additional details of exemplary nanopore sequencing devices and methods of operating the devices that can be used in conjunction with the present disclosure can be found in U.S. Provisional Patent Application Nos. 63/200,868 and 63/169,041 (International Patent Application Numbers PCT/US2021/038125 and PCT/US2022/020395), the entirety of each of the disclosures is incorporated herein by reference.

It is to be understood that any features of the device and/or of the array disclosed herein may be combined together in any desirable manner and/or configuration. Further, it is to be understood that any features of the method of using the device may be combined together in any desirable manner. Moreover, it is to be understood that any combination of features of this method and/or of the device and/or of the array may be used together, and/or may be combined with any of the examples disclosed herein. Still further, it is to be understood that any feature or combination of features of any of the devices and/or of the arrays and/or of any of the methods may be combined together in any desirable manner, and/or may be combined with any of the examples disclosed herein.

It should be appreciated that all combinations of the foregoing concepts and additional concepts discussed in greater detail below are contemplated as being part of the inventive subject matter disclosed herein and may be used to achieve the benefits and advantages described herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1A:
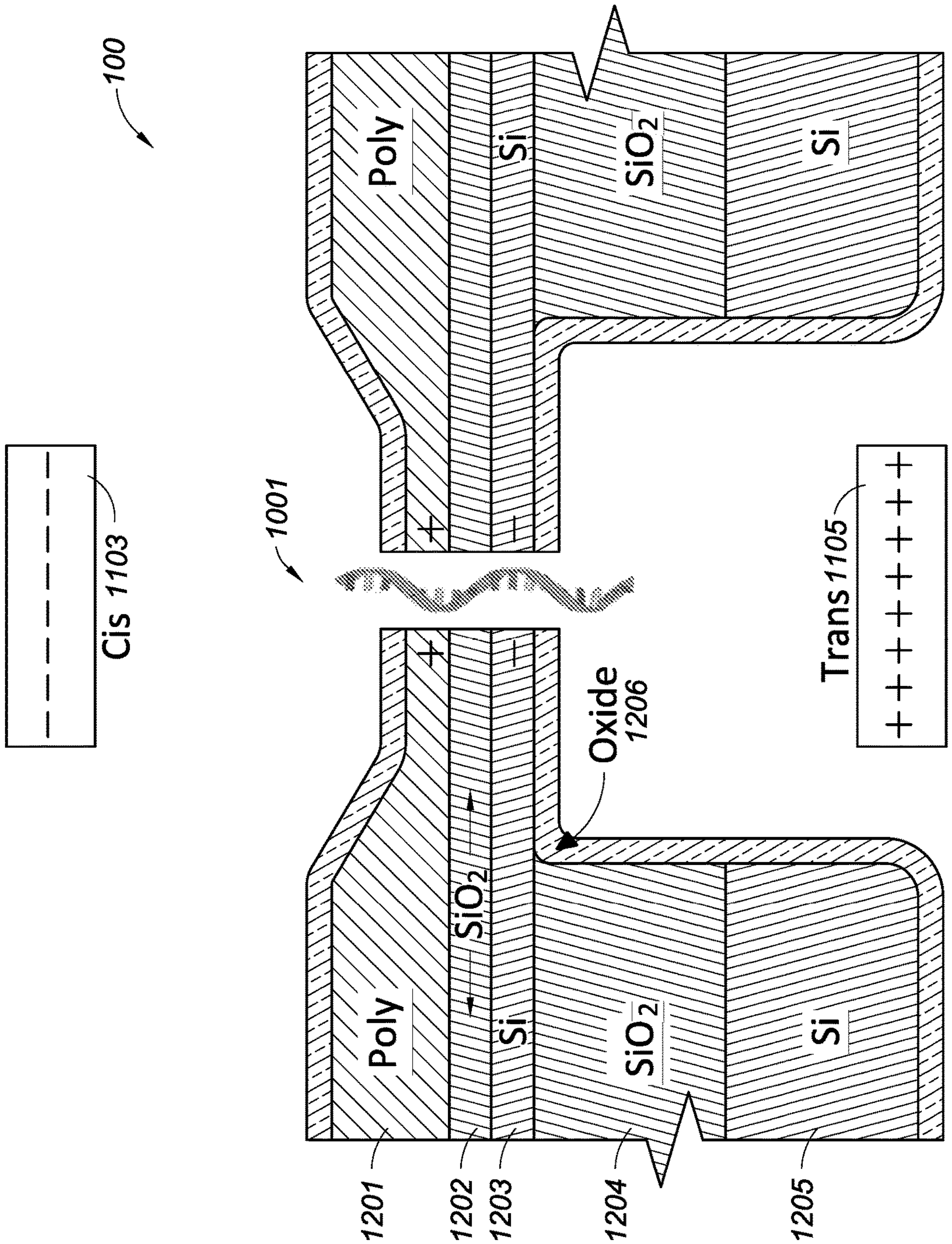
FIG. 1A schematically illustrates an example of DNA translocation through a solid-state nanopore.

All patents, applications, published applications and other publications referred to herein are incorporated herein by reference to the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

Definitions

All technical and scientific terms used herein have the same meaning as commonly understood to one of ordinary skill in the art to which this disclosure belongs unless clearly indicated otherwise.

As used herein, the singular forms “a”, “and”, and “the” include plural referents unless the context clearly dictates otherwise. Thus, for example, reference to “a sequence” may include a plurality of such sequences, and so forth.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the term “operably connected” refers to a configuration of elements, wherein an action or reaction of one element affects another element, but in a manner that preserves each element’s functionality.

As used herein, the term “membrane” refers to a non-permeable or semi-permeable barrier or other sheet that separates two liquid/gel chambers (e.g., a cis well and a fluidic cavity) which can contain the same compositions or different compositions therein. The permeability of the membrane to any given species depends upon the nature of the membrane. In some examples, the membrane may be non-permeable to ions, to electric current, and/or to fluids. For example, a lipid membrane may be impermeable to ions (i.e., does not allow any ion transport therethrough), but may be at least partially permeable to water (e.g., water diffusivity ranges from about 40 μm/s to about 100 μm/s). For another example, a synthetic/solid-state membrane, one example of which is silicon nitride, may be impermeable to ions, electric charge, and fluids (i.e., the diffusion of all of these species is zero). Any membrane may be used in accordance with the present disclosure, as long as the membrane can include a transmembrane nanoscale opening and can maintain a potential difference across the membrane. The membrane may be a monolayer or a multilayer membrane. A multilayer membrane includes two or more layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure (e.g., a biomimetic material).

An example membrane that is made from the material of biological origin includes a monolayer formed by a bolalipid. Another example membrane that is made from the material of biological origin includes a lipid bilayer. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture that is substantially perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid-state materials and can form a solid-state membrane, and others of these materials can form a thin liquid film or membrane. The solid-state membrane can be a monolayer, such as a coating or film on a supporting substrate (i.e., a solid support), or a freestanding element. The solid-state membrane can also be a composite of multilayered materials in a sandwich configuration. Any material not of biological origin may be used, as long as the resulting membrane can include a transmembrane nanoscale opening and can maintain a potential difference across the membrane. The membranes may include organic materials, inorganic materials, or both. Examples of suitable solid-state materials include, for example, microelectronic materials, insulating materials (e.g., silicon nitride ($Si_3N_4$), aluminum oxide ($Al_2O_3$), hafnium oxide ($HfO_2$), tantalum pentoxide ($Ta_2O_5$), silicon oxide ($SiO_2$), etc.), some organic and inorganic polymers (e.g., polyamide, plastics, such as polytetrafluoroethylene (PTFE), or elastomers, such as two-component addition-cure silicone rubber), and glasses. In addition, the solid-state membrane can be made from a monolayer of graphene, which is an atomically thin sheet of carbon atoms densely packed into a two-dimensional honeycomb lattice, a multilayer of graphene, or one or more layers of graphene mixed with one or more layers of other solid-state materials. A graphene-containing solid-state membrane can include at least one graphene layer that is a graphene nanoribbon or graphene nanogap, which can be used as an electrical sensor to characterize the target polynucleotide. It is to be understood that the solid-state membrane can be made by any suitable method, for example, chemical vapor deposition (CVD). In an example, a graphene membrane can be prepared through either CVD or exfoliation from graphite. Examples of suitable thin liquid film materials that may be used include diblock copolymers or triblock copolymers, such as amphiphilic PMOXA-PDMS-PMOXA ABA triblock copolymers.

As used herein, the term “nanopore” is intended to mean a hollow structure discrete from, or defined in, and extending across the membrane. The nanopore permits ions, electric current, and/or fluids to cross from one side of the membrane to the other side of the membrane. For example, a membrane that inhibits the passage of ions or water-soluble molecules can include a nanopore structure that extends across the membrane to permit the passage (through a nanoscale opening extending through the nanopore structure) of the ions or water-soluble molecules from one side of the membrane to the other side of the membrane. The diameter of the nanoscale opening extending through the nanopore structure can vary along its length (i.e., from one side of the membrane to the other side of the membrane), but at any point is on the nanoscale (i.e., from about 1 nm to about 100 nm, or to less than 1000 nm). Examples of the nanopore include, for example, biological nanopores, solid-state nanopores, and biological and solid-state hybrid nanopores. In some embodiments, a nanopore refers to a pore having an opening with a diameter at its most narrow point of about 0.3 nm to about 2 nm. For example, a nanopore may be a solid-state nanopore, a graphene nanopore, an elastomer nanopore, or may be a naturally-occurring or recombinant protein that forms a tunnel upon insertion into a bilayer, thin film, membrane, or solid-state aperture, also referred to as a protein pore or protein nanopore herein (e.g., a transmembrane pore). If the protein inserts into the membrane, then the protein is a tunnel-forming protein.

As used herein, the term "biological nanopore" is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, the term "polypeptide nanopore" is intended to mean a protein/polypeptide that extends across the membrane, and permits ions, electric current, polymers such as DNA or peptides, or other molecules of appropriate dimension and charge, and/or fluids to flow therethrough from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin, *Mycobacterium smegmatis* porin A (MspA), gramicidin A, maltoporin, OmpF, OmpC, PhoE, Tsx, F-pilus, aerolysin, etc. The protein α-hemolysin is found naturally in cell membranes, where it acts as a pore for ions or molecules to be transported in and out of cells. *Mycobacterium smegmatis* porin A (MspA) is a membrane porin produced by Mycobacteria, which allows hydrophilic molecules to enter the bacterium. MspA forms a tightly interconnected octamer and transmembrane beta-barrel that resembles a goblet and contains a central pore.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof such as locked nucleic acids (LNA) and peptide nucleic acids (PNA). A polynucleotide may be a single stranded sequence of nucleotides, such as RNA or single stranded DNA, a double stranded sequence of nucleotides, such as double stranded DNA, or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA, LNA, or PNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, the term "solid-state nanopore" is intended to mean a nanopore whose structure portion is defined by a solid-state membrane and includes materials of non-biological origin (i.e., not of biological origin). A solid-state nanopore can be formed of an inorganic or organic material. Solid-state nanopores include, for example, silicon nitride nanopores, silicon dioxide nanopores, and graphene nanopores.

The nanopores disclosed herein may be hybrid nanopores. A "hybrid nanopore" refers to a nanopore including materials of both biological and non-biological origins. An example of a hybrid nanopore includes a polypeptide-solid-state hybrid nanopore and a polynucleotide-solid-state nanopore.

The application of the potential difference across a nanopore may force the translocation of a nucleic acid through the nanopore. One or more signals are generated that correspond to the translocation of the nucleotide through the nanopore. Accordingly, as a target polynucleotide, or as a mononucleotide or a probe derived from the target polynucleotide or mononucleotide, transits through the nanopore, the current across the membrane changes due to base-dependent (or probe dependent) blockage of the nanopore constriction, for example. The signal from that change in current can be measured using any of a variety of methods. Each signal is unique to the species of nucleotide(s) (or probe) in the nanopore, such that the resultant signal can be used to determine a characteristic of the polynucleotide. For example, the identity of one or more species of nucleotide(s) (or probe) that produces a characteristic signal can be determined.

As used herein, the term "nanopore sequencer" refers to any of the devices disclosed herein that can be used for nanopore sequencing. In the examples disclosed herein, during nanopore sequencing, the nanopore is immersed in examples of the electrolyte disclosed herein and a potential difference is applied across the membrane. In an example, the potential difference is an electric potential difference or an electrochemical potential difference. An electrical potential difference can be imposed across the membrane via a voltage source that injects or administers current to at least one of the ions of the electrolyte contained in the cis well or one or more of the trans wells. An electrochemical potential difference can be established by a difference in ionic composition of the cis and trans wells in combination with an electrical potential. The different ionic composition can be, for example, different ions in each well or different concentrations of the same ions in each well.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, voltage, conductance, or a transverse electrical effect. An "electronic current" or "electric current" refers to a flow of electric charge. In an example, an electrical signal may be an electric current passing through a nanopore, and the electric current may flow when an electric potential difference is applied across the nanopore.

The aspects and examples set forth herein and recited in the claims can be understood in view of the above definitions.

Sequencing Using a Nanopore

Polynucleotides may be sequenced using a nanopore unit cell, or a nanopore sensor, based on electrical responses. In some embodiments, such unit cell may include a nanopore, a flow chamber containing a liquid, one or more electrodes, and an electronic circuit for measurement. In some cases, the nanopore may be a solid-state nanopore as illustrated in FIG. 1A. In some cases, the nanopore may be a solid-state nanopore directly formed as a nanoscale opening in a membrane (e.g., silicon based, graphene, or polymer membrane). A polynucleotide may be dissolved in the liquid, e.g., an electrolyte. In some embodiments, application of a voltage via the one or more electrodes results in a driving force and/or a change in the electrical conditions that are suitable for driving translocation of the polynucleotide through the nanopore, for example from the "cis" side to the "trans" side, or vice versa. As the polynucleotide translocates through the nanopore, the polynucleotide may modulate the electrical properties of the nanopore, such that the nucleobase sequence of the polynucleotide can be identified. For example, the electrical current through the nanopore or the electrical resistance at the nanopore may be a function of the identity of the nucleobase of the polynucleotide at or near the nanopore. FIG. 1A schematically illustrates an example of a polynucleotide 1001 translocating through a solid-state nanopore device 100. The solid-state nanopore device 100 includes a silicon substrate 1205; a silicon dioxide layer 1204 formed on the silicon substrate 1205; and a stack of polysilicon 1201, silicon dioxide 1202 and silicon 1203 materials formed on the silicon dioxide layer 1204. A silicon oxide layer 1206 may be grown on the surfaces of the device 100 and may insulate the device 100. A nano-scale opening is formed in the stack of polysilicon 1201, silicon dioxide 1202 and silicon 1203 materials, allowing the polynucleotide 1001 to pass through. The device 100 may further include a cis electrode 1103 and a trans electrode 1105 for application of a voltage across the device 100. An electrolyte may be filled in the chambers between the electrodes 1103 and 1105 and the silicon oxide layer 1206. The polynucleotide 1001 may be negatively charged in the electrolyte and may thus be driven through the nano-scale opening from the cis side to the trans side or vice versa when a voltage difference between the cis electrode 1103 and the trans electrode 1105 is applied.

Figure 1B:
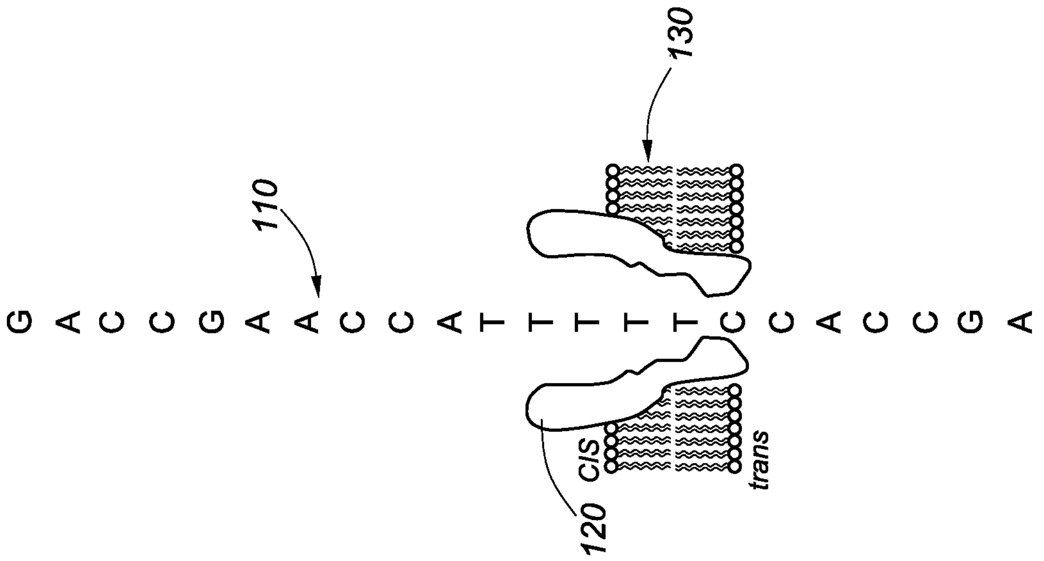
FIG. 1B schematically illustrates an example of DNA translocation through a protein nanopore.

In some cases, the nanopore may be a biological nanopore formed of peptides or polynucleotides and deposited in a lipid bilayer or a polymer membrane, e.g., a synthetic polymeric membrane. In an example shown in FIG. 1B, a protein nanopore 120 is deposited in a lipid bilayer 130. A single-stranded DNA 110 is passing, from the "cis" side, through the nanopore 120, to the "trans" side, or vice versa. Applying a voltage across the "cis" side to the "trans" side results in an ionic current through the nanopore. When a nucleotide of the DNA 110 is in or near the nanopore, it may result in a unique ionic current blockade at the nanopore 120, and therefore a unique nanopore resistance depending on the identity of the nucleotide. By measuring the ionic current or the nanopore resistance, the nucleotide at or near the nanopore can be identified.

In other embodiments, the DNA 110 may not pass through the nanopore 120. A unique tag or label for a nucleotide in the DNA 110 may pass through the nanopore 120. In one example, a tag or label of the nucleotide may be a particular sequence combination of nucleotides. When the tag or label is in or near the nanopore, it may result in a unique ionic current blockade at the nanopore, and therefore a unique nanopore resistance depending on the identity of the molecule of interest. By measuring the ionic current or the nanopore resistance, the tag or label at or near the nanopore, and therefore the corresponding nucleotide, can be identified.

Although embodiments herein describe determining a signal level by determining the ionic current through the nanopore, embodiments also include alone or in combination determining the signal level by measuring other electrical characteristics of the cis/trans nanopore cell. For example, in other embodiments, a signal level is determined by the voltage potential at a specified area or component of the cis/trans nanopore cell. For example, in other embodiments, a signal level is determined by the electrical impedance at a specified area or component of the cis/trans nanopore cell. For example, in other embodiments, a signal level is determined by the conductivity/resistance of the nanopore membrane.

In other embodiments, sequencing of a target polynucleotide may involve nanopore sensing of (1) a single-stranded portion of the target polynucleotide; (2) a nucleic acid duplex of a portion of the target polynucleotide; (3) a label or tag that can be tethered or untethered to the target polynucleotide; or any combination thereof.

In some embodiments, multiple such nanopore unit cells may be arranged in an array, and each unit cell or each nanopore sensor may be individually accessed by a logic circuit.

Measurement Circuit for Nanopore Sequencing

In some embodiments, a nanopore array is formed of an array of biochemical sensors, e.g., an array of nanopore unit cells described above. In some embodiments, a nanopore array can be used to perform long read DNA sequencing. A characteristic feature of a nanopore array is G-base per second per square centimeter of a chip. In some embodiments, to achieve higher data rate, the density of nanopores in a 2D array is increased. In some embodiments, a 2D readout circuit is used to take measurements from a 2D nanopore array.

Figure 2:
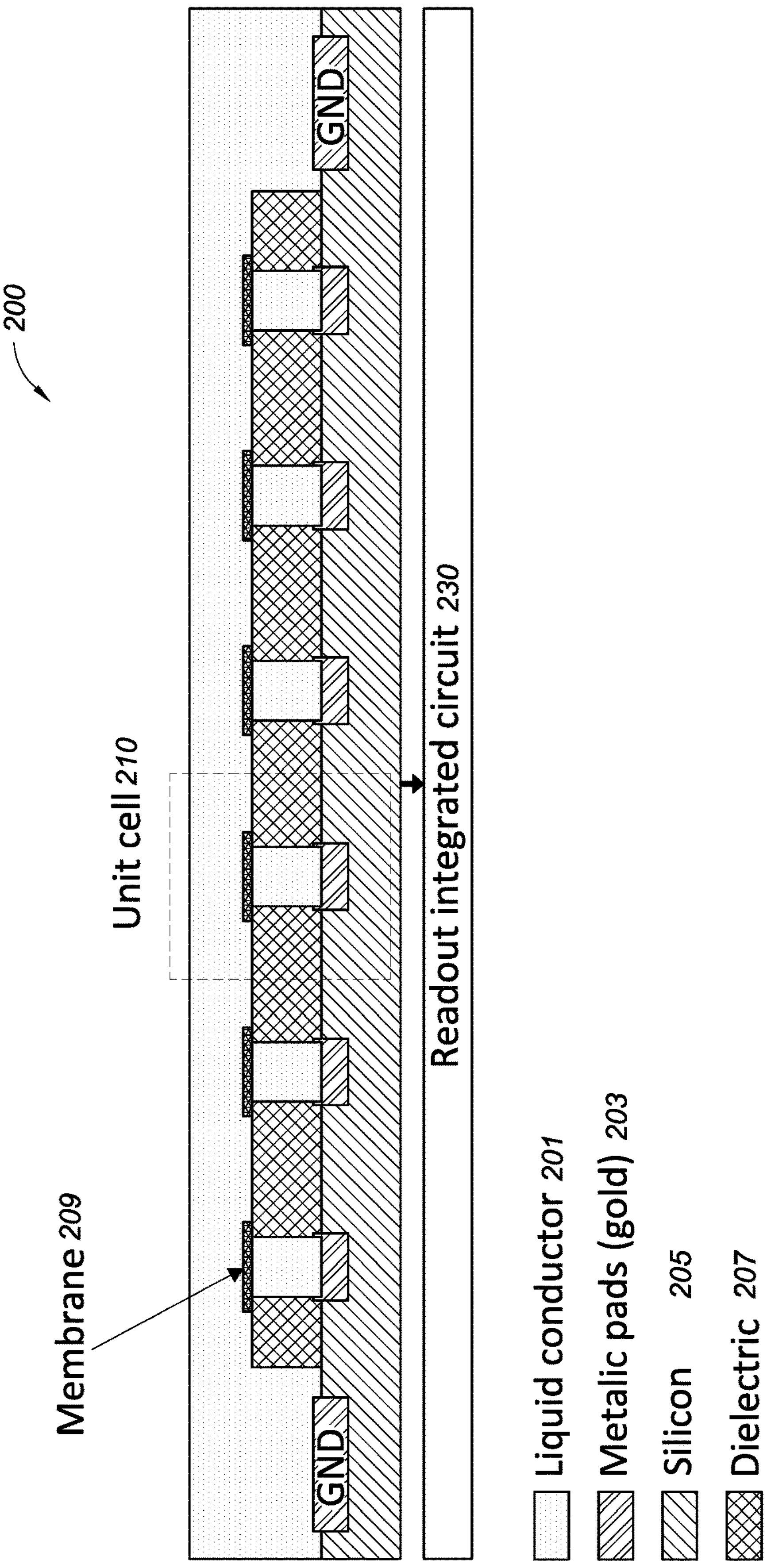
FIG. 2 schematically illustrates an example integration of nanopore array with a readout integrated circuit (ROIC).

FIG. 2 schematically illustrates an example integration of nanopore array 200 with a readout integrated circuit (ROIC). In one example, the nanopore array 200 is formed on a silicon substrate 205, which is integrated with a CMOS readout integrated circuit 230. In one example, the nanopore array 200 includes a plurality of nanopore unit cells 210. Individual nanopore unit cells 210 may be separated by dielectric 207. In one example, the nanopore array 200 may be a 2D high density nanopore array. In some embodiments, each nanopore unit cell 210 is operably connected to a common ground via an electrode (e.g., a metallic pad 203 shown in FIG. 2) in the unit cell 210. In some embodiments, each nanopore unit cell 210 contains a conductor liquid 201 and a membrane 209 for inserting a nanopore. Each nanopore unit cell 210 may include a nanopore shown and described in connection with FIG. 1A or FIG. 1B.

Figure 3:
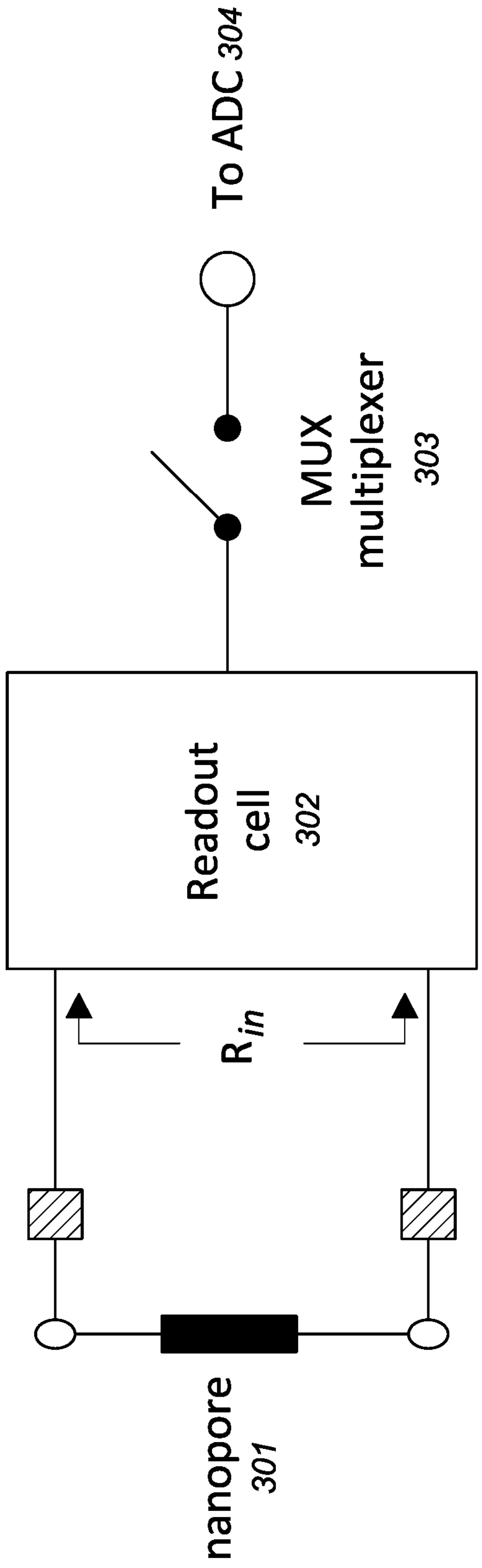
FIG. 3 schematically illustrates one of the nanopore unit cells shown in FIG. 2.

FIG. 3 schematically illustrates one of the nanopore unit cells shown in FIG. 2. Each nanopore unit cell reads data from a nanopore 301 using a corresponding readout cell 302. The readout cell 302 may be coupled to a multiplexer (MUX) 303, which may be coupled to an analog-to-digital converter (ADC) 304. The readout cell 302 may have an equivalent input resistance $R_{in}$.

Figure 4:
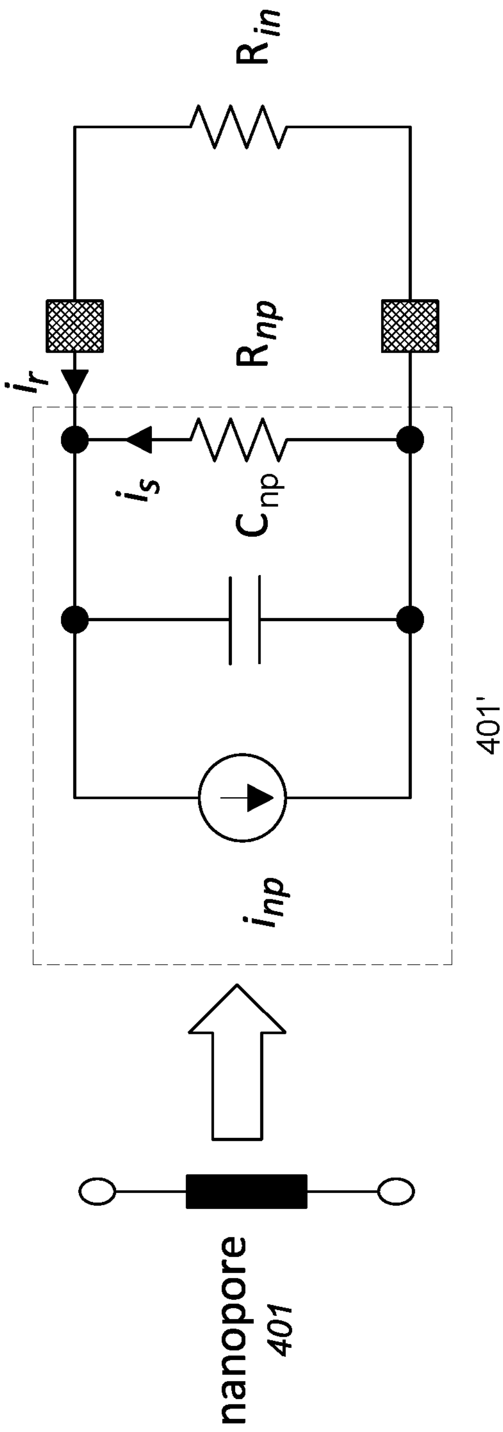
FIG. 4 schematically illustrates an equivalent circuit of the unit cell shown in FIG. 3.
Figure 4:
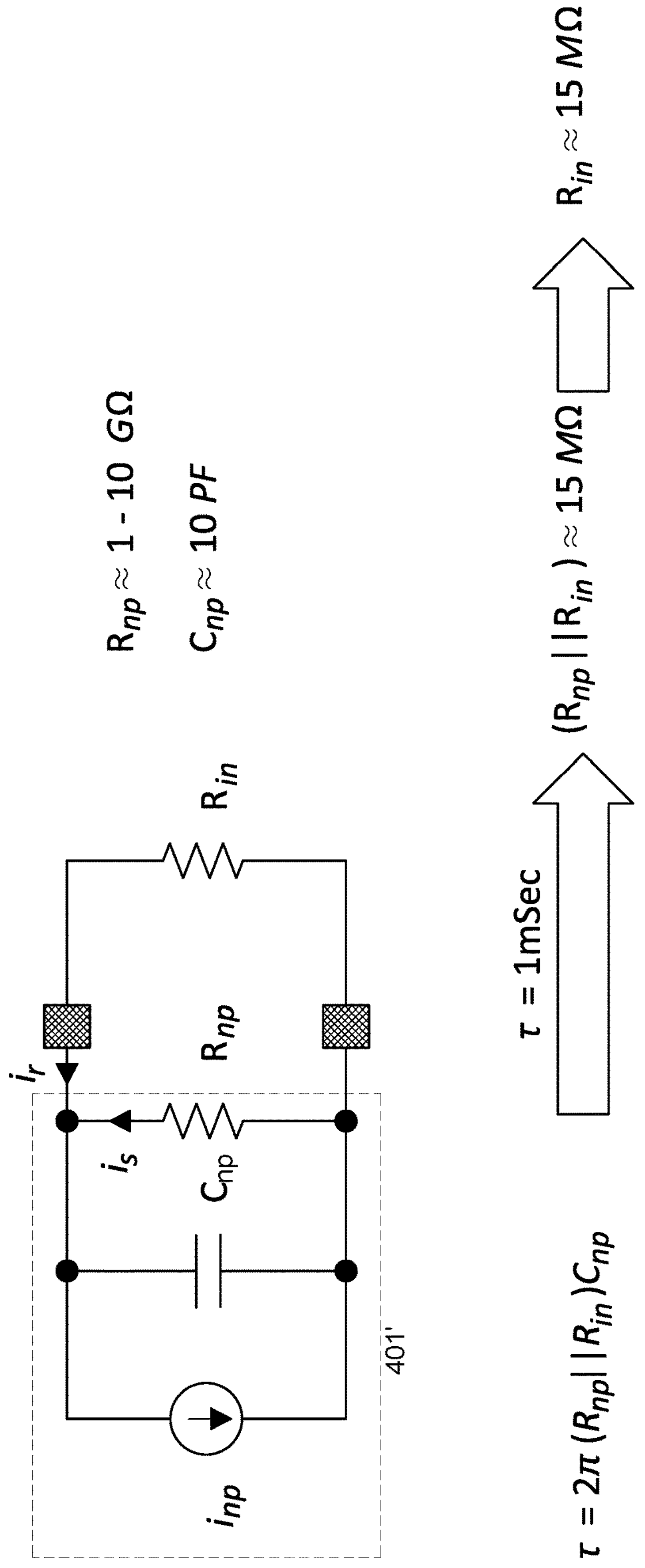

FIG. 4 schematically illustrates an equivalent circuit of the unit cell shown in FIG. 3. A nanopore 401 may have an equivalent circuit diagram 401' that includes a current source $i_{np}$, a capacitance $C_{np}$ and a resistance $R_{np}$. In a preferred embodiment, input resistance of the readout cell $R_{in}$ is small enough to allow a fast readout. In one example, if $R_{in} \ll R_{np}$, unit cell response time may be determined by the input resistance of the readout cell. Example values of resistances, capacitance and circuit time constant are shown in FIG. 4 (Continued).

Apply Different Bias Voltages to Different Unit Cells

In some applications of nanopore sequencing, the mode of operation in a nanopore unit cell can be changed over the course of sequencing. For example, the mode of operation can be changed after a "read" event (i.e., measurement of one nucleobase). Changing the mode of operation may involve changing the bias voltage applied between the cis side and the trans side of the nanopore.

Figure 5:
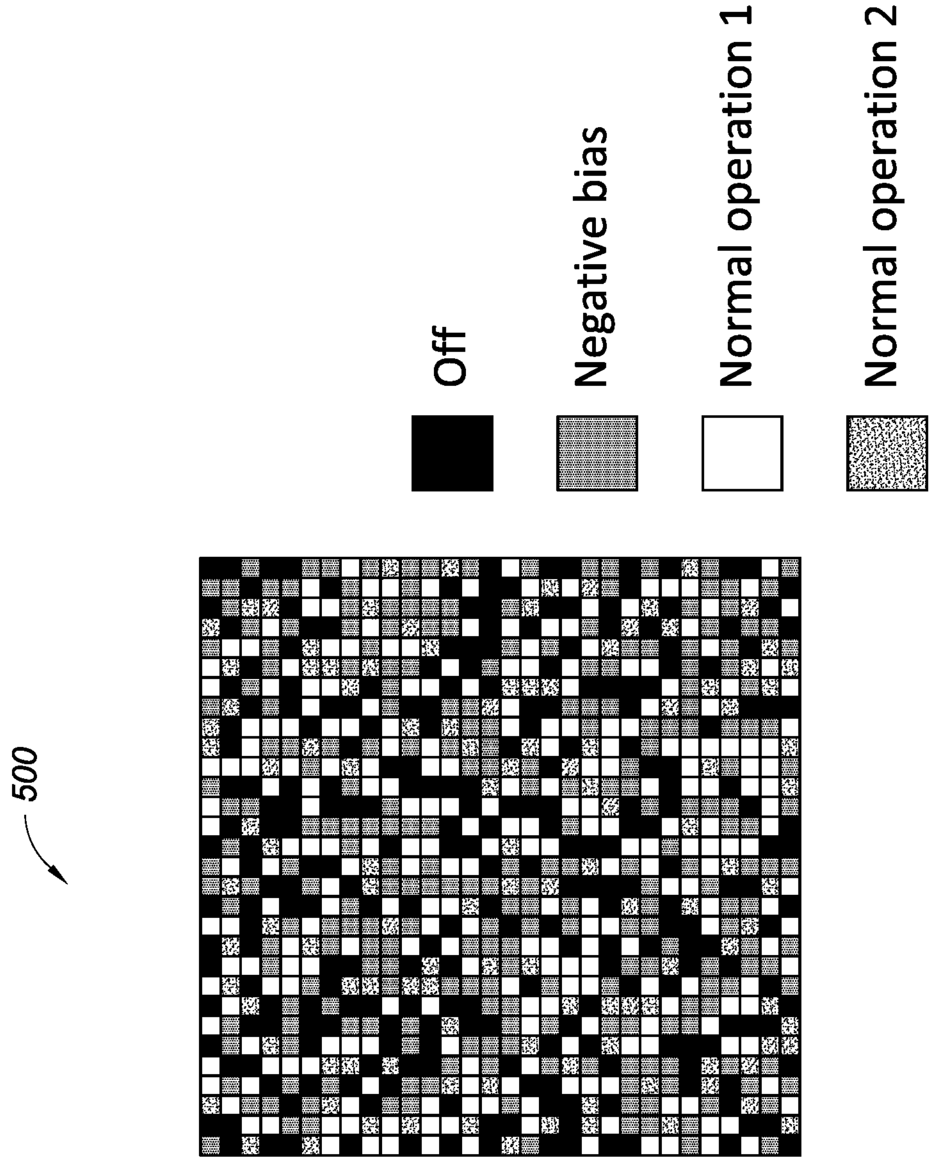
FIG. 5 schematically illustrates an example ensemble of the modes of operation in a 2D array of nanopore unit cells.

In some embodiments, at least three modes of operation are used in nanopore sequencing: The "normal operation" mode may be used for identifying the nucleobases in a polynucleotide, while applying a certain bias voltage waveform (e.g., an alternating current waveform, a direct current waveform, or a pulsed direct current waveform) to a nanopore unit cell. In some embodiments, more than one "normal operation" modes may be used. For example, "normal operation 1" and "normal operation 2" may use different values of bias voltage or different waveforms of bias voltage for different read levels. In some embodiments, the "negative bias" mode may refer to applying a reverse bias in comparison to the DC bias used in the "normal operation mode.". In some embodiments, the "negative bias" mode may be used to reverse the translocation direction of the polynucleotide as compared to the "normal operation" mode or to disengage and remove the polynucleotide from the nanopore. The "negative bias" mode may be used for removing the polynucleotide from the nanopore, in one example. The "off" mode may refer to applying a certain bias voltage that can create an open circuit condition to a nanopore unit cell. The "off" mode may be used to stop the unit cell from draining any current and to ensure that the unit cell is not impacting neighboring unit cells. For example, the "off" mode may be used when the cell is not properly functioning for one or more of the following reasons: membrane failure, pore insertion failure, and/or template polynucleotide capture failure. In an example ensemble of the modes of operation in a 2D array of nanopore unit cells 500 illustrated in FIG. 5, four modes of operation, "off" mode, "negative bias" mode, "normal operation 1" mode and "normal operation 2" mode, are shown at various nanopore unit cells. As shown in FIG. 5, at any moment in time, different unit cells may be at different stages of sequencing. Different unit cells in an array may operate independently from each other. The sequencing in different unit cells may progress at different velocities and may be controlled independently, for example by a field-programmable gate array (FPGA). In general, the sequencing in different unit cells may be controlled by a controller implemented in hardware, software, or both, such as CPUs, GPUs, FPGA, microcontroller, or microprocessors.

In some embodiments, the applied voltage value or waveform of each of the "normal operation" modes, "off" mode or "negative bias" mode can be chosen depending on the experimental conditions and requirements. In some embodiments, the applied voltage value or waveform of each of the "normal operation" modes, "off" mode or "negative bias" mode can vary over time. In some embodiments, the applied voltage value or waveform of each of the "normal operation" modes, "off" mode or "negative bias" mode can be controlled independently in each unit cell. In some examples, the normal operation modes may use positive voltage biases. For example, the positive biases may include several different values, such as 40 mV, 60 mV, 80 mV, etc.

To independently control or address each unit cell, in some embodiments, each of the nanopore unit cells in a nanopore array may have its own trans electrode but may share a common cis electrode. In some embodiments, each of the nanopore unit cells in a nanopore array may have its own cis electrode but may share a common trans electrode. In some embodiments, each of the nanopore unit cells in a nanopore array may have its own cis electrode and trans electrode. In some embodiments, each of the nanopore unit cells in a nanopore array may share a common cis electrode and a common trans electrode.

The array may have any suitable number of nanopore unit cells. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, about 10000000 or more nanopore unit cells. In some instances, the array comprises at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, at least 1000000 or at least 10000000 nanopore unit cells. In some cases, the array can include individually addressable nanopore unit cells at a density of at least about 500, 600, 700, 800, 900, 1000, 10,000, 100,000 or 1,000,000 unit cells per $mm^2$.

Since the various modes and applied voltages allow the polynucleotide to move back and forth through the nanopore, in different embodiments, a polynucleotide molecule may be sequenced 1 time, 2 times, 3 times, 4 times, 5 times, 6 times, 7 times, 8 times, 9 times, 10 times, 12 times, 14 times, 16 times, 18 times, 20 times, 25 times, 30 times, 35 times, 40 times, 45 times, 50 times, or more. In some embodiments, a polynucleotide molecule is sequenced between about 1 time and 10 times, between about 1 time and 5 times, or between about 1 time and 3 times. A higher level of base-calling accuracy may be achieved by combining data collected from sequencing a polynucleotide molecule more than once.

Figure 6:
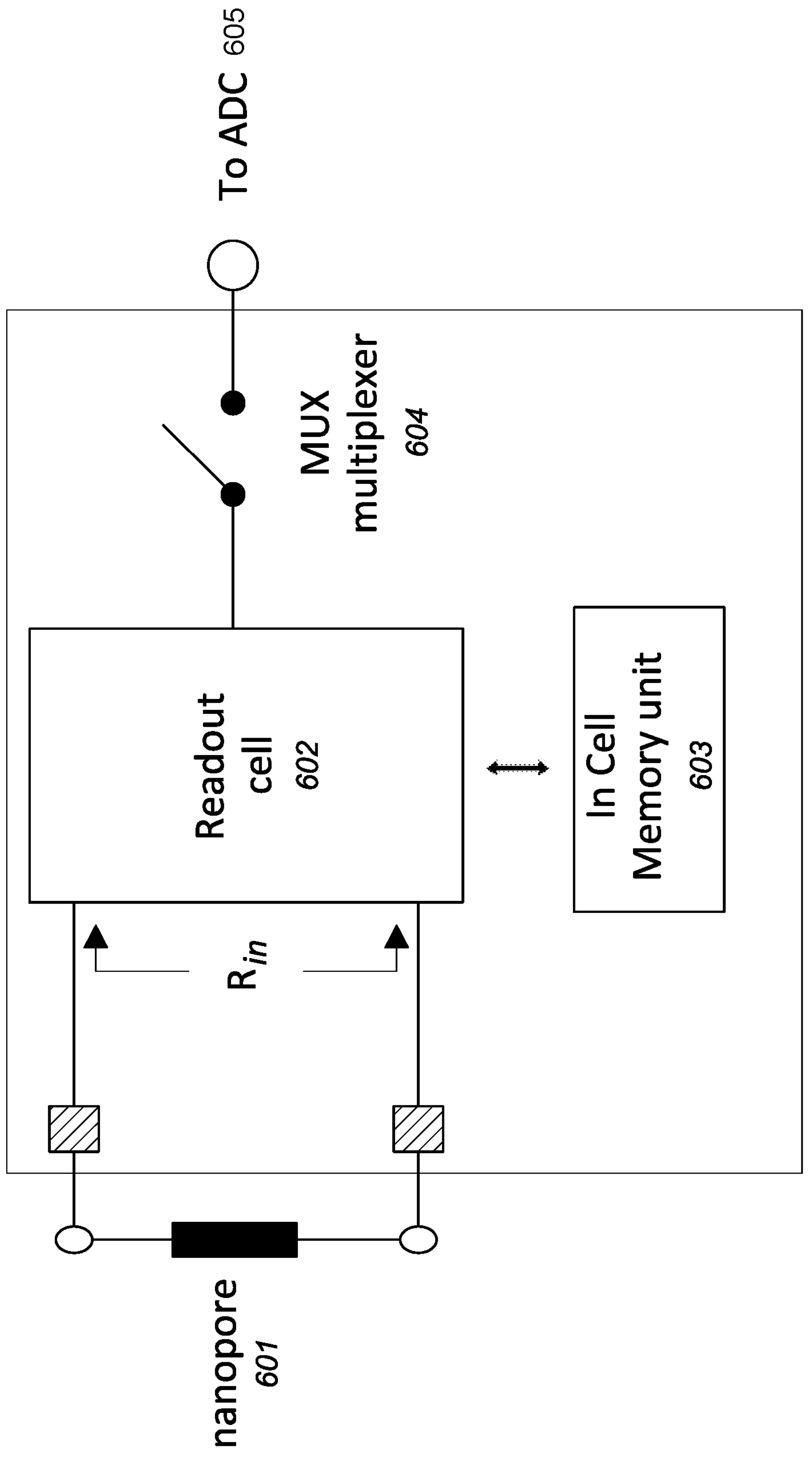
FIG. 6 schematically illustrates an embodiment of a nanopore unit cell including a memory unit.

In some embodiments, an "in-cell" memory unit is included in a nanopore unit cell in order to control the mode of operation of the unit cell. An embodiment of a nanopore unit cell including a memory unit 603 is shown in FIG. 6. As shown in FIG. 6, a readout cell (readout electronic circuit) 602 measures signal from the nanopore 601. The memory unit 603 can be operably connected with the readout cell 602 of the nanopore unit cell and can store the state of the nanopore unit cell. The memory unit can allow selectivity in terms of the mode of operation in the nanopore unit cell. The readout cell 602 may be connected to a multiplexer (MUX) 604, which is connected to an analog-to-digital converter 605.

Figure 7:
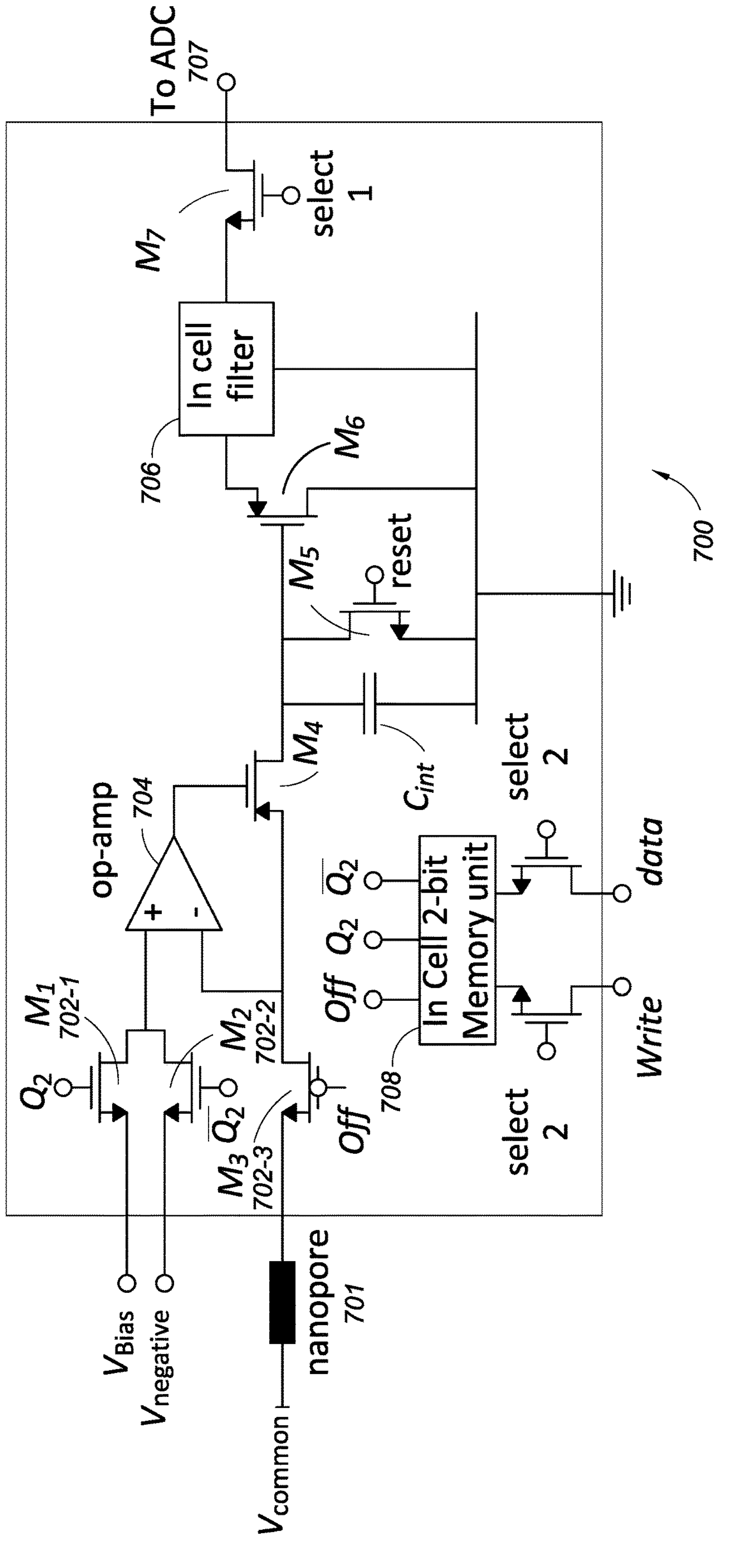
FIG. 7 schematically illustrates an example circuit design relating to the nanopore unit cell shown in FIG. 6.

FIG. 7 schematically illustrates an example circuit design relating to the readout cell and the memory unit in the nanopore unit cell shown in FIG. 6. According to the example circuit design 700 shown in FIG. 7, the three modes of operation, i.e., "normal operation", "negative bias" and "off", may be achieved as follows.

To achieve the "normal operation" mode, a voltage $V_{bias}$ may be operably connected to the positive input terminal of an operational amplifier (op-amp) 704 in the unit cell, by keeping the switch M1 (702-1) on and keeping the switch M2 (702-2) off. To achieve the "negative bias" mode, the switch M1 (702-1) that connects $V_{bias}$ to the op-amp may be switched off, and a negative bias $V_{negative}$ may be connected to the positive input terminal of the op-amp by switching on the switch M2 (702-2). To achieve the "off" mode, the M3 (702-3) switch may be turned on, while the M1 (702-1) and M2 (702-2) switches are kept off, such that the nanopore is disconnected from the readout cell (readout electronic circuit). Signal measured from the nanopore sequencing unit cell 701 may be fed to the negative input terminal of the operational amplifier 704 via the M3 (702-3) switch. The nanopore sequencing unit cell 701 may include a nanopore, for example a nanopore shown in FIG. 1A or FIG. 1B. The turning on and turning off of the M1 (702-1), M2 (702-2), and M3 (702-3) switches may be controlled by the combination of the voltage values labeled as "$Q_2$", "$\overline{Q_2}$" and "Off" in FIG. 7. The combination of voltage values "$Q_2$", "$\overline{Q_2}$" and "Off" may be output from the memory unit 708 depending on the stored state of the nanopore unit cell and one or more inputs to the memory unit. In some embodiments, the nanopore unit cell may further include an analog-to-digital converter 707, and/or an in-cell filter 706 (e.g., RC filter bank). In some embodiments, the same select signal may be used for "select 1" and "select 2". Any of the switches/gates shown in FIG. 7 may be implemented as a solid-state switch, such as a transistor, e.g., a metal-oxide-semiconductor field-effect transistor (MOSFET).

In some embodiments, the memory unit used in the example of FIG. 7 can include one or more SRAM, DRAM, NAND gate, NOR gate, other logic gates, electronic switches, latch circuits, capacitors, registers, or any combination thereof. In some embodiments, a memory unit can store any number of bits representing the state of an individual nanopore unit cell. For example, an individual nanopore unit cell may be operated in three modes, e.g., "normal" mode, "negative" mode and "off" mode, and the three modes may be represented in the memory unit by using two bits.

Example Sequencing Systems and Methods

In one aspect, the disclosed technology relates to a device for sequencing polynucleotides, comprising: a sequencing cell comprising a nanopore for sensing a polynucleotide; an electronic circuit configured to measure an electrical response in the sequencing cell, the electronic circuit comprising an operational amplifier; and a memory unit configured to store a state of the sequencing cell.

In some embodiments, the device includes at least one voltage source operably connected to the positive input terminal of the operational amplifier via at least one switch.

In some embodiments, the at least one switch is operably connected to at least some output terminals of the memory unit.

In some embodiments, the sequencing cell is operably connected to the negative input terminal of the operational amplifier via a gate.

In some embodiments, the gate is operably connected to at least some output terminals of the memory unit.

In some embodiments, outputs of the memory unit depend in part on the stored state of the sequencing cell.

In some embodiments, the stored state of the sequencing cell is associated with a previous electrical response in the sequencing cell.

In some embodiments, the nanopore is an opening in a protein or nucleic acid structure deposited in a lipid or polymer membrane, or wherein the nanopore is an opening in a solid-state structure.

In some embodiments, the electrical response in the sequencing cell is modulated by: nucleotides in the polynucleotide near the sensing zone of the nanopore, labels on nucleotides in the polynucleotide near the sensing zone of the nanopore, nucleotides being incorporated to the polynucleotide, labels on nucleotides being incorporated to the polynucleotide, or any combination thereof.

In another aspect, the disclosed technology relates to a method for sequencing polynucleotides, comprising: providing a polynucleotide to a sequencing cell comprising a nanopore; providing, based on outputs of a memory unit, at least one voltage input to the sequencing cell from at least one voltage source; and measuring an electrical response in the sequencing cell by way of an electronic circuit, wherein the electrical response depends on the identity of one or more nucleotides of polynucleotide within or near the nanopore.

In some embodiments, outputs of the memory unit depend in part on a stored state of the sequencing cell.

In some embodiments, the stored state of the sequencing cell is associated with a previous electrical response in the sequencing cell.

In some embodiments, the electrical response measured by the electronic circuit is an ionic current through the nanopore or equivalents thereof.

In some embodiments, the electrical response is modulated by: nucleotides in the polynucleotide near the sensing zone of the nanopore, labels on nucleotides in the polynucleotide near the sensing zone of the nanopore, nucleotides being incorporated to the polynucleotide, labels on nucleotides being incorporated to the polynucleotide, or any combination thereof.

In some embodiments, the method further includes providing an electrolyte to the sequencing cell prior to providing the polynucleotide.

In yet another aspect, the disclosed technology relates to a system for sequencing polynucleotides, comprising: a common cis well associated with a common cis electrode; and a plurality of sequencing units comprising an electrolyte, each of the plurality of sequencing units comprising: a trans well associated with a trans electrode; a sequencing cell comprising a nanopore for sensing a polynucleotide, the nanopore fluidically connecting the trans well to the common cis well; an electronic circuit configured to measure an electrical response in the sequencing cell; and a memory unit configured to store a state of the sequencing cell.

In some embodiments, for at least some of the plurality of sequencing units, the electronic circuit comprises an operational amplifier, the positive input terminal of the operational amplifier operably connected to at least one voltage source via at least one switch controlled by outputs of the memory unit.

In some embodiments, for at least some of the plurality of sequencing units, the sequencing cell is operably connected to the negative input terminal of the operational amplifier via a gate controlled by outputs of the memory unit.

In some embodiments, for at least some of the plurality of sequencing units, outputs of the memory unit depend in part on the stored state of the sequencing cell.

In some embodiments, for at least some of the plurality of sequencing units, the stored state of the sequencing cell is associated with a previous electrical response in the sequencing cell.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to “one example”, “another example”, “an example”, and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such value or sub-range were explicitly recited. For example, a range from about 2 nm to about 20 nm should be interpreted to include not only the explicitly recited limits of from about 2 nm to about 20 nm, but also to include individual values, such as about 3.5 nm, about 8 nm, about 18.2 nm, etc., and sub-ranges, such as from about 5 nm to about 10 nm, etc. Furthermore, when “about” and/or “substantially” are/is utilized to describe a value, this is meant to encompass minor variations (up to +/−10%) from the stated value.

While several examples have been described in detail, it is to be understood that the disclosed examples may be modified. Therefore, the foregoing description is to be considered nonlimiting.

While certain examples have been described, these examples have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure.

Features, materials, characteristics, or groups described in conjunction with a particular aspect, or example are to be understood to be applicable to any other aspect or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a claimed combination can, in some cases, be excised from the combination, and the combination may be claimed as a sub-combination or variation of a sub-combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some examples, the actual steps taken in the processes illustrated and/or disclosed may differ from those shown in the figures. Depending on the example, certain of the steps described above may be removed or others may be added. Furthermore, the features and attributes of the specific examples disclosed above may be combined in different ways to form additional examples, all of which fall within the scope of the present disclosure. Also, the separation of various system components in the implementations described above should not be understood as requiring such separation in all implementations, and it should be understood that the described components and systems can generally be integrated together in a single product or packaged into multiple products. For example, any of the components for an energy storage system described herein can be provided separately, or integrated together (e.g., packaged together, or attached together) to form an energy storage system.

For purposes of this disclosure, certain aspects, advantages, and novel features are described herein. Not necessarily all such advantages may be achieved in accordance with any particular example. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain examples include, while other examples do not include, certain features, elements, and/or steps. Thus, such conditional language is not generally intended to imply that features, elements, and/or steps are in any way required for one or more examples or that one or more examples necessarily include logic for deciding, with or without user input or prompting, whether these features, elements, and/or steps are included or are to be performed in any particular example.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

Language of degree used herein, such as the terms "approximately," "about," "generally," and "substantially" represent a value, amount, or characteristic close to the stated value, amount, or characteristic that still performs a desired function or achieves a desired result.

The scope of the present disclosure is not intended to be limited by the specific disclosures of preferred examples in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A device for sequencing polynucleotides, comprising:

at least one voltage source; and at least two sequencing units, each comprising:

- a sequencing cell comprising a nanopore for sensing a polynucleotide;
- an electronic circuit configured to measure an electrical response in the sequencing cell, the electronic circuit comprising an operational amplifier, a positive input terminal of the operational amplifier operably connected to said at least one voltage source via at least one switch; and
- a memory unit configured to store a state of the sequencing cell, at least some output terminals of the memory unit operably connected to the at least one switch.

2. The device of claim 1, wherein the respective sequencing cell in each sequencing unit is operably connected to a negative input terminal of the respective operational amplifier via a gate in said sequencing unit.

3. The device of claim 2, wherein the respective gate in said sequencing unit is operably connected to at least some output terminals of the respective memory unit in said sequencing unit.

4. The device of claim 1, wherein outputs of the respective memory unit of each sequencing unit depend in part on the stored state of the respective sequencing cell in said sequencing unit.

5. The device of claim 1, wherein the stored state of the respective sequencing cell of each sequencing unit is associated with a previous electrical response in said sequencing cell.

6. The device of claim 1, wherein the respective nanopore of each sequencing unit is an opening in a protein or nucleic acid structure deposited in a lipid or polymer membrane, or wherein the respective nanopore of each sequencing unit is an opening in a solid-state structure.

7. The device of claim 1, wherein the electrical response in the respective sequencing cell of each sequencing unit is modulated by: nucleotides in the respective polynucleotide near a sensing zone of the respective nanopore in said sequencing unit, labels on nucleotides in the respective polynucleotide near the sensing zone of the respective nanopore in said sequencing unit, nucleotides being incorporated to the respective polynucleotide in said sequencing unit, labels on nucleotides being incorporated to the respective polynucleotide in said sequencing unit, or any combination thereof.

8. A method for sequencing polynucleotides, comprising:

- providing a polynucleotide to the respective sequencing cell of a sequencing unit in the device of claim 1;
- providing, based on outputs of the respective memory unit in said sequencing unit, at least one voltage input to the respective sequencing cell from the at least one voltage source; and
- measuring the electrical response in the respective sequencing cell by way of the respective electronic circuit in said sequencing unit, wherein the electrical response depends on the identity of one or more nucleotides of the polynucleotide within or near the respective nanopore of the respective sequencing cell.

9. The method of claim 8, wherein outputs of the respective memory unit depend in part on the stored state of the respective sequencing cell.

10. The method of claim 9, wherein the stored state of the respective sequencing cell is associated with a previous electrical response in the respective sequencing cell.

11. The method of claim 8, wherein the electrical response measured by the respective electronic circuit is an ionic current through the respective nanopore or equivalents thereof.

12. The method of claim 8, wherein the electrical response in the respective sequencing cell is modulated by: nucleotides in the polynucleotide near a sensing zone of the respective nanopore, labels on nucleotides in the polynucleotide near the sensing zone of the respective nanopore, nucleotides being incorporated to the polynucleotide, labels on nucleotides being incorporated to the polynucleotide, or any combination thereof.

13. The method of claim 8, further comprising providing an electrolyte to the respective sequencing cell prior to providing the polynucleotide.

14. A device for sequencing polynucleotides, comprising at least two sequencing units, each comprising:

- a sequencing cell comprising a nanopore for sensing a polynucleotide;
- an electronic circuit configured to measure an electrical response in the sequencing cell, the electronic circuit comprising an operational amplifier, a negative input terminal of the operational amplifier operably connected to the sequencing cell via a gate; and
- a memory unit configured to store a state of the sequencing cell, at least some output terminals of the memory unit operably connected to the gate.

15. The device of claim 14, wherein outputs of the respective memory unit of each sequencing unit depend in part on the stored state of the respective sequencing cell in said sequencing unit.

16. The device of claim 14, wherein the stored state of the respective sequencing cell of each sequencing unit is associated with a previous electrical response in said sequencing cell.

17. The device of claim 14, wherein the respective nanopore of each sequencing unit is an opening in a protein or nucleic acid structure deposited in a lipid or polymer membrane, or wherein the respective nanopore of each sequencing unit is an opening in a solid-state structure.

18. The device of claim 14, wherein the electrical response in the respective sequencing cell of each sequencing unit is modulated by: nucleotides in the respective polynucleotide near a sensing zone of the respective nanopore in said sequencing unit, labels on nucleotides in the respective polynucleotide near the sensing zone of the respective nanopore in said sequencing unit, nucleotides being incorporated to the respective polynucleotide in said sequencing unit, labels on nucleotides being incorporated to the respective polynucleotide in said sequencing unit, or any combination thereof.

* * * * *